United States Patent [19]
Young et al.

[11] B 3,990,476
[45] Nov. 9, 1976

[54] HIGH TEMPERATURE GAS CHROMATOGRAPH VALVE
[75] Inventors: Einar T. Young, Newtown Square; Robert L. Tinklepaugh, Malvern, both of Pa.
[73] Assignee: Sun Oil Company of Pennsylvania, Philadelphia, Pa.
[22] Filed: Dec. 2, 1974
[21] Appl. No.: 528,756
[44] Published under the second Trial Voluntary Protest Program on February 3, 1976 as document No. B 528,756.

[52] U.S. Cl. ............................ 137/625.46; 251/58; 92/37
[51] Int. Cl.² ...................... G01N 1/00; F16K 11/02
[58] Field of Search ................ 137/625.46; 251/58; 92/37

[56] References Cited
UNITED STATES PATENTS

| 2,198,965 | 4/1940 | Habig et al. | 92/37 X |
| 2,363,410 | 11/1944 | Gill | 92/37 X |
| 3,216,326 | 11/1965 | Rice et al. | 137/625.46 X |
| 3,223,123 | 12/1965 | Young | 137/625.46 |
| 3,329,167 | 7/1967 | Boettcher et al. | 137/625.46 |
| 3,386,338 | 6/1968 | King | 251/58 X |
| 3,486,731 | 12/1969 | Magnani et al. | 251/58 |

Primary Examiner—Henry T. Klinksiek
Attorney, Agent, or Firm—J. Edward Hess; Donald R. Johnson; Gary V. Pack

[57] ABSTRACT

A rotary control valve which is actuated by a steel bellows mechanism for use in a gas chromatograph. The steel bellows mechanism changes the valve positions as required by the gas chromatograph operation. An improved spring design provides an even pressure to the disc rotating against the valve body as well as allowing this pressure to be varied. Use of steel bellows and the proper materials for construction of the control valve will allow complete installation in the oven of a gas chromatograph for operation at a maximum temperature of 600° F.

4 Claims, 4 Drawing Figures

HIGH TEMPERATURE GAS CHROMATOGRAPH VALVE

The control valve disclosed and claimed herein is designed for use in the gas chromatography apparatus disclosed and claimed in copending application Ser. No. 528,755, filed of even date herewith, and now U.S. Pat. No. 3,910,765.

This invention relates to a gas chromatograph valve and actuator, and more particularly to a rotary gas chromatograph valve actuated by steel bellows, having an improved mechanism for pressing the rotating disc on the valve body.

The control valve employed in this invention is in one embodiment an improved design of the valve disclosed in Young U.S. Pat. No. 3,223,123, Dec. 14, 1965. This earlier valve as well as other valves found in the prior art cannot withstand the higher temperatures required to vaporize fluids with high boiling points. This invention makes it possible to heat the control valve to the testing temperature used by the chromatograph and to heat the test fluid to the testing temperature before it is sampled, thereby enabling better control of the test.

Another problem with the control valves in the prior art is their slow switching speeds and actuating means. Electric motors often take too long to switch control valves because of the time it takes to begin rotating and to transmit the rotation through a gear arrangement. During this slow actuation time, the entire sample volume is not injected into the system at the same time, thereby resulting in reduced chromatograph efficiency.

The disclosed invention minimizes this problem by utilizing an improved spring design and steel bellows to actuate the valve. The spring design provides greater pressure between the fixed valve body and the rotating disc, thereby decreasing the possibility of fluid leaks. The steel bellows are able to actuate the valve almost instantaneously. An added advantage of the steel bellows is the ability to use the carrier gas to provide the pressure needed to operate the bellows, thereby eliminating the need for supplementary pressure systems. This advantage is especially important if the chromatograph is used at a remote site. Use of the proper metals in the spring design enables the valve to withstand operating temperatures as high as 500° to 600°F. Since the steel bellows is made without a rubber diaphragm, it too can withstand these temperatures.

This invention also offers an improvement over the cited Young patent in the control of the angle through which the valve drive shaft rotates, providing more accurate alignment of channels and fluid passages in the valve. Because of this improvement, the channels in the rotating disc can be made smaller, thereby increasing the surface area between channels and further minimizing the possibility of leaks. Also, the sample volume is reduced in size allowing use of small diameter column separators which result in faster analysis of the test fluid and more accurate plotting of test results.

An object of this invention is to provide an improved "rotary" type control valve for use in a chromatograph.

Another object is to accomplish the foregoing object in an efficient manner having quick actuating times and controlled volumes of the sample fluid.

A further object is to accomplish the foregoing objects while being able to withstand temperatures as high as 500° to 600°F.

The objects of this invention are accomplished, briefly, in the following manner:

A generally cylindrical valve body containing a plurality of fluid passages terminating on the circular end face of the valve body and a disc member with a plurality of channels recessed on its surface is typically provided, the face of the disc member being positioned in engagement with the valve body face. The valve body face and passages interact with the disc member and channels, injecting the sample fluid into the carrier gas flow as well as switching the carrier gas flow from its flushing or cleaning mode to its testing mode in a similar manner as disclosed in the above Young patent. A generally flat (in its relaxed position) disc spring is used to provide pressure to the disc member for engagement with the valve body face. A pair of steel bellows actuate the control valve, utilizing the carrier gas for the required operating pressure.

Further objects and advantages of this invention will become obvious in the following detailed description of the invention taken in conjunction with the accompanying drawings wherein.

Figure 1:
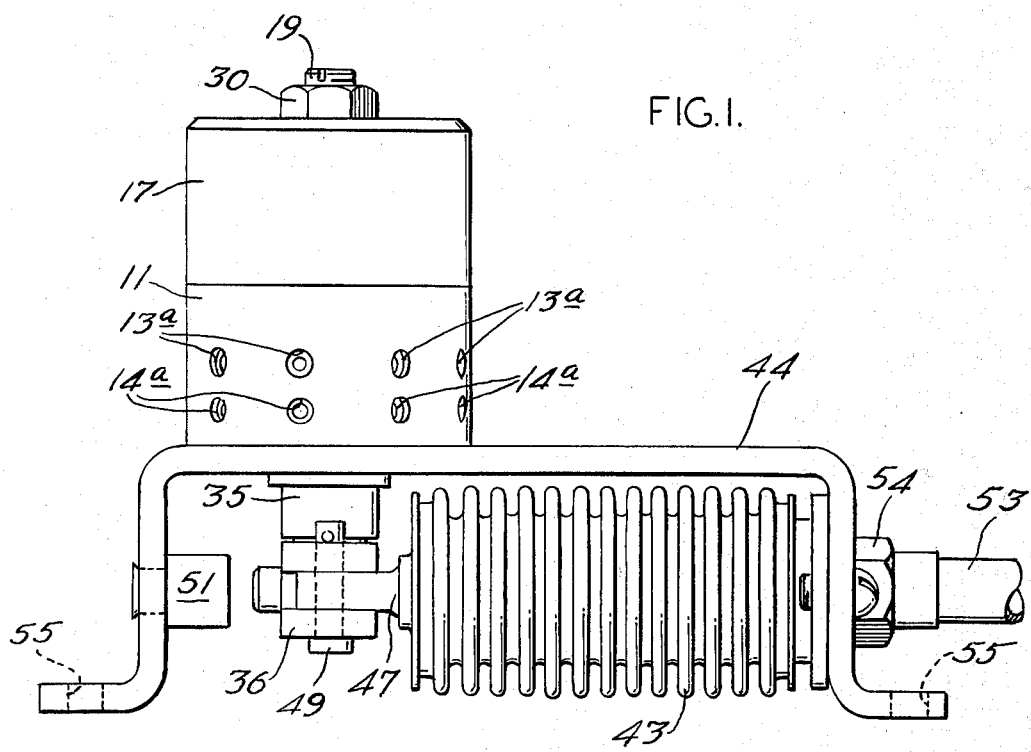
FIG. 1 is a pictorial view depicting the placement of the control valve on the frame encasing the steel bellows actuating system.
Figure 2:
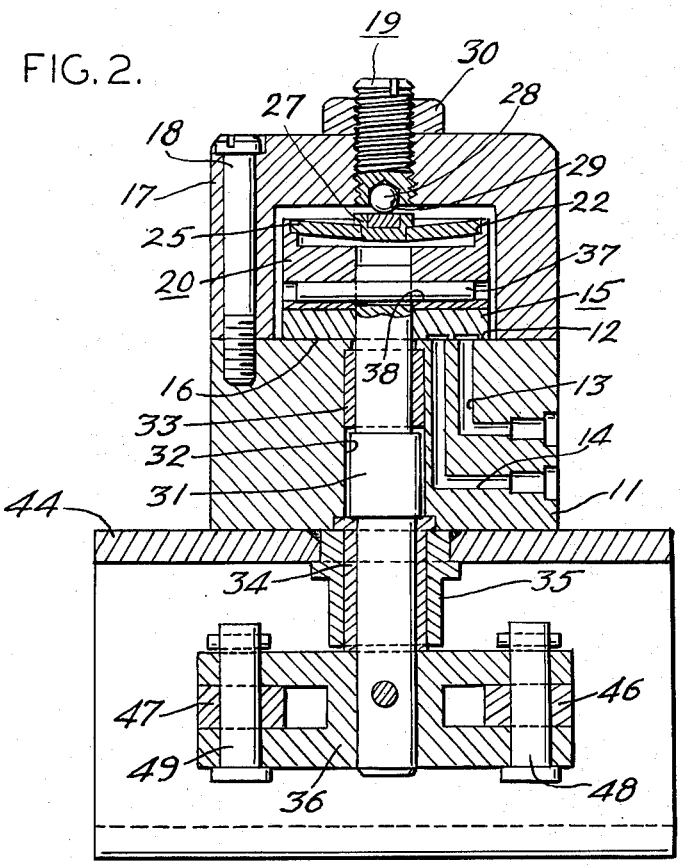
FIG. 2 is a vertical section through a control valve according to this invention.
Figure 3:
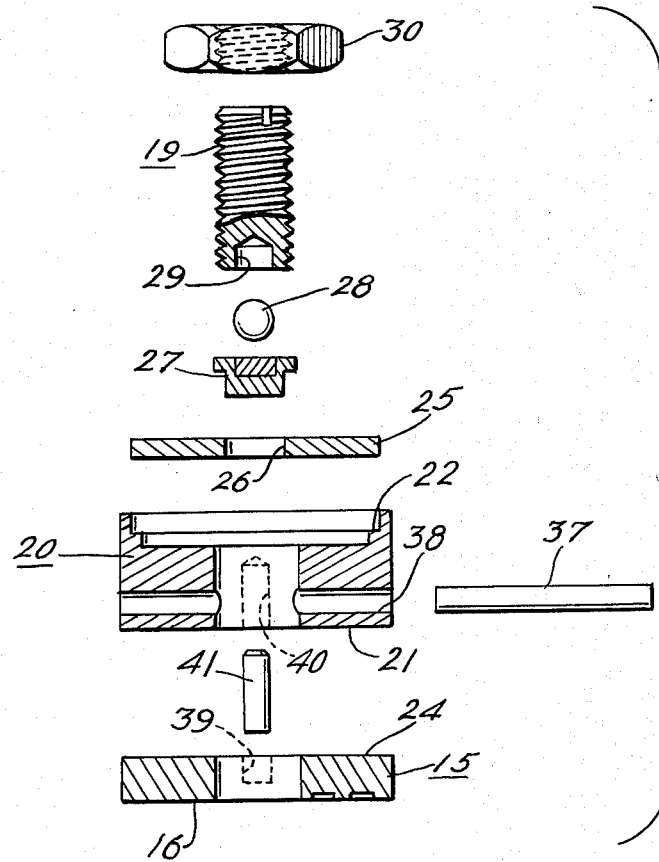
FIG. 3 is an exploded vertical section through the internal parts of a control valve according to this invention, without the drive shaft.

Refer now to FIGS. 1, 2 and 3. A generally cylindrical valve body 11 has a circular planar end face 12 which is polished smooth and optically flat. Body 11 has therein fourteen fluid passages, which travel from the outside circumference of the valve body 11, through valve body 11, to the valve body end face 12. Only two internal fluid passages, 13 and 14, are shown in FIG. 2. Possible port locations for the internal passages are shown in FIG. 1 as ports 13a and 14a. An embodiment depicting the preferred location of the terminal ends of the internal passages on valve body end face 12 is disclosed in the Young Patent.

A generally cylindrical disc member 15 has a circular face 16 polished smooth and optically flat. Circular face 16 contains channels located in positions such that the terminal ends of the internal passages on valve body end face 12 are connected to each other through these channels. The connection pattern can be varied by rotation of disc member 15. A preferred embodiment of the exact placement of the channels and the rotation positions is depicted and explained in detail in the aforementioned Young Patent.

A domed valve cover 17 holds the internal valve assembly together and prevents foreign matter from entering the internal valve structure. Valve cover 17 is held securely to valve body 11 by three connecting bolts 18 extending through valve cover 17 and threadedly attached to valve body 11. The three connecting bolts are located equidistantly around the outside circumference of valve cover 17, however, only one connecting bolt 18 is shown in FIG. 2.

Disc member 15 is held in sealed relation with the main valve body 11 by pressure means which will now be described. The following internal assembly cooperates between disc member 15 and set screw 19. A generally cylindrical pressure plate 20, having a flat lower face 21 and a shoulder 22 extending entirely around the circumference of the top of pressure plate 20, rests on upper face 24 of disc member 15. Spring disc 25 is generally cylindrical shaped with a circular opening 26 in its central portion and rests on shoulder 22 of pressure plate 20. Insert disc 27 is generally cylindrical shaped with its lower diameter small enough to fit into opening 26. The upper diameter of insert disc 27 is larger than the diameter of opening 26, thereby allowing insert disc 27 to rest on spring disc 25. A ball bearing 28 rests on the upper surface of insert disc 27 and is partially encased within recess 29 of set screw 19.

When the internal parts of the valve are assembled, set screw 19 is threaded through valve cover 17 and is rotated to apply force to ball bearing 28 which is transmitted through spring disc 25 and pressure plate 20 to disc member 15. Once the proper pressure required to seal disc face 16 against valve body end face 12 is obtained, lock-nut 30 is threaded onto set screw 19 and tightened against valve cover 17 to prevent set screw 19 from loosening.

Disc member 15, while being held in sealed contact with body face 12, is mounted for rotation with respect thereto. A drive shaft 31 is journaled for rotation in bore 32 of valve body 11, the center line of the shaft coinciding with the axis of the bore. Drive shaft 31 extends through valve body 11, disc 15 and into pressure plate 20.

Valve bearing 33, located inside bore 32, and shaft bearing 34, secured in the bearing retainer 35, hold drive shaft 31 securely in valve body 11. The external end of drive shaft 31 extends away from valve body 11 and is secured to the center of valve actuating lever 36.

The control valve is actuated by rotation of drive shaft 31. This rotating motion is transmitted to disc 15 by the means now to be described. A connecting pin 37 extends transversely completely through the internal end of drive shaft 31 and through bore 38 of pressure plate 20. Upper face 24 of disc member 15 and lower face 21 of pressure plate 20 each have a recessed vertical opening, 39 and 40 respectively, equidistant from the center axis of each cylinder, enabling driving pin 41 to rest in both disc 15 and pressure plate 20. Driving pin 41 and the friction between lower face 21 of pressure plate 20 and the upper face 24 of disc member 15 forces disc member 15 to rotate when drive shaft 31 rotates pressure plate 20.

Figure 4:
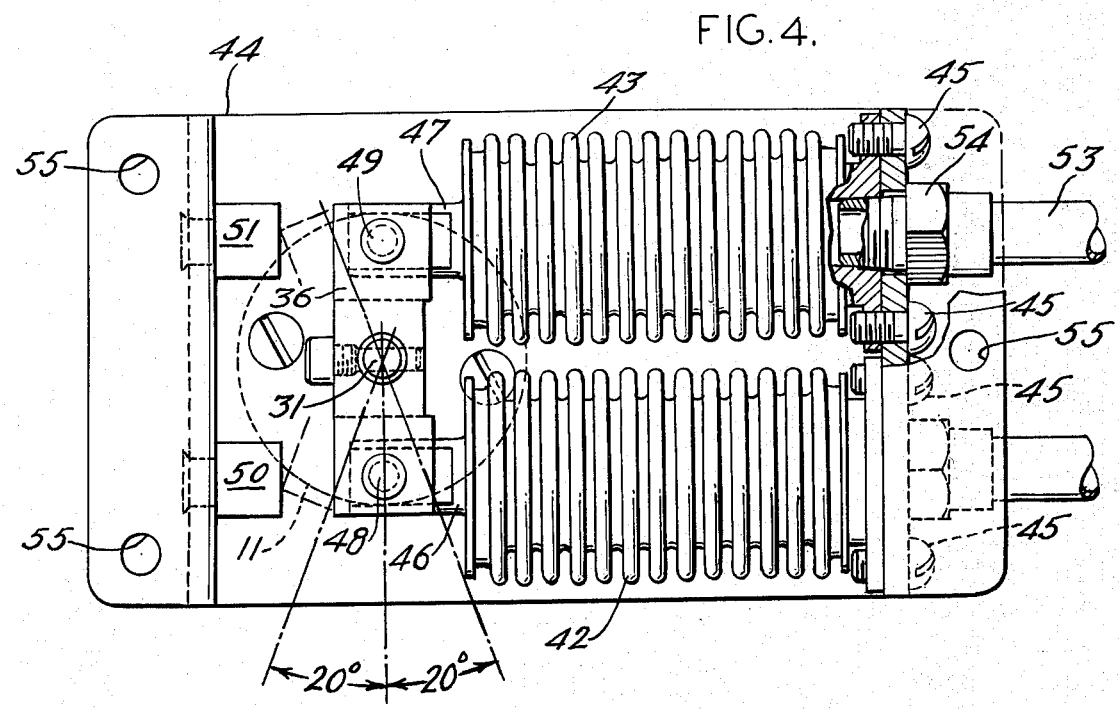
FIG. 4 is a view of the steel bellows actuating system and their connection to the control valve with a partial section.

Now refer to FIG. 4. Two steel bellows, 42 and 43, are employed to rotate lever 36, thereby actuating the valve. Steel bellows 42 and 43 are rigidly connected to support frame 44 by screws 45. Push rods 46 and 47 are rigidly attached to steel bellows 42 and 43 respectively, and are pivotally connected to either end of lever 36 by connecting pin 48 and 49 respectively. Stop blocks 50 and 51 are securely attached to support frame 44 at a predetermined distance from each respective push rod in order that drive shaft 31 is rotated the correct distance for proper valve operation. Steel bellows 42 and 43 are connected to their respective source of pressure (not shown) by tubing 53 coupled to the base of each steel bellows by coupling 54. Opening 55 is provided for easy mounting of support frame 44 on a frame for a chromatograph.

While the above arrangement of steel bellows is the preferred design, it is understood that other bellows arrangements can be constructed to accomplish the same results. One variation of the preferred design is to relocate one of the steel bellows on the opposite side of the lever 36 and relocating the stops 50 and 51. In this manner larger steel bellows can be used and the bellows push rods can be located closer to the valve drive shaft 31. This arrangement reduces the distance the bellows must expand, thereby increasing the useful life of each bellow.

In the preferred embodiment of this invention, the passages in valve body 11 and the channels in disc member 15 are positioned as disclosed in the Young Patent. This design uses only two switching positions, 40° apart as seen in FIG. 4. Stop blocks 50 and 51 are positioned the precise distance from push rods 44 and 45 respectively such that when one steel bellows is activated, lever 36 swings in a 40° arc and when the other steel bellows is activated, lever 36 rotates 40° in the opposite direction. This rotation motion is transferred to rotating disc member 15 through drive shaft 31, connecting pin 37, pressure plate 20, and driving pin 41.

Use of set screw 19 enables variable pressures to be used on disc member 15. A chromatograph can be used with various processes, each having different kinds of gases at various pressures. When testing gases from a process using high pressures, set screw 19 can be rotated to increase pressure on disc member 15, thereby minimizing the chance of leaks. However, if the sample comes from a process using lower pressures, set screw 19 can be rotated to decrease the pressure on disc member 15, thereby reducing the pressure required to actuate steel bellows 42 and 43, and increasing the life of the entire valve and actuating system.

The force exerted by set screw 19 is applied to one point through ball bearing 28 and then distributed to the entire disc member 15 through insert disc 27, spring disc 25, and pressure plate 20. Spring disc 25 is instrumental in distributing the "point" force from ball bearing 28 evenly to disc member 15.

Because of the 14 passageways in valve body 11, many various switching patterns can be developed, thereby providing much versatility to any chromatograph. The aforementioned Young patent discloses several valve connection configurations for testing samples and flushing the system between tests.

The invention claimed is:

1. A valve for injecting fluid samples into a gas chromatograph and for switching the flow directions of the gas flowing in the chromatograph, said valve designed so that it can withstand the high temperature environment in which the chromatograph is contained and to have improved sealing means to prevent gas leaks, thereby enabling more accurate chromatograph tests to be conducted, and comprising:
  a. a valve body having a planar face, and having therein a plurality of fluid passages initiating from the outer circumference of the valve body and terminating on the planar face;
  b. a disc member positioned adjacent to the planar face of the valve body and having a plurality of channels in the side adjacent to the valve body planar face, said channels arranged to connect selected terminal ends of the fluid passages in the valve body depending on the position of said disc member with respect to the planar face of the valve body;
  c. a drive shaft which passes through the valve body and the disc member and is rotatably secured in the valve body and secured to the disc member so that the disc member can be rotated by rotating the drive shaft;
d. valve cover means, secured to the valve body, for covering the disc member and the planar face of the valve body;
e. a set screw threaded through the top of the valve cover means transversely to the planar face of the valve body, so that greater force is applied to the disc member as said set screw is rotated toward the valve body; and
f. means distributing the point force from the set screw to the outside edge of the disc member so that force is applied evenly to the entire face of the disc in contact with the valve body planar face, thereby minimizing the leakage of fluid from the valve.

2. The valve recited in claim 1, wherein the distributing means comprises:
a. a pressure plate which rests on top of the disc member, and having a shoulder extending around the circumference of the top of said pressure plate;
b. a spring disc having its outer edge engaging the shoulder of the pressure plate and its center portion in communication with the set screw.

3. The valve recited in claim 1, further including means for actuating said valve, which can be constructed to withstand the high temperature enviroment of the gas chromatograph, and comprising:
a. a frame, on which the valve is mounted;
b. an actuating lever affixed at its center portion to the drive shaft;
c. a pair of chambers logitudinally expansible by gas pressure, each chamber mounted on one end to the frame and having a push rod on its other end, with each push rod pivotally connected to an end of the actuating lever.

4. The valve recited in claim 3, wherein the expansible chambers are steel bellows which can withstand the high temperatures encountered by gas chromatograph systems.

* * * * *